United States Patent [19]
Fraser et al.

[11] Patent Number: 4,787,752
[45] Date of Patent: Nov. 29, 1988

[54] LIVE COMPONENT TEMPERATURE CONDITIONING DEVICE PROVIDING FAST TEMPERATURE VARIATIONS

[75] Inventors: Douglas S. Fraser, Bloomingtion; Taylor N. Thompson, Jr., Kingston, both of N.Y.

[73] Assignee: FTS Systems, Inc., Stone Ridge, N.Y.

[21] Appl. No.: 922,520

[22] Filed: Oct. 24, 1986

[51] Int. Cl.[4] ............................................. G01N 25/00
[52] U.S. Cl. ...................................... 374/45; 374/57; 324/158 F
[58] Field of Search ................... 374/45, 57; 73/865.6; 324/158 P, 158 F, 73 PC; 165/30, 35, 27, 61, 64

[56] References Cited

U.S. PATENT DOCUMENTS

| | | | |
|---|---|---|---|
| 2,749,050 | 6/1956 | Booth | 165/35 |
| 3,710,251 | 1/1973 | Hagge et al. | 324/158 F |
| 3,724,235 | 4/1973 | Carpigiani | 165/61 |
| 3,979,671 | 9/1976 | Meeker et al. | 324/158 F |
| 4,011,903 | 3/1977 | Harbin et al. | 165/27 |
| 4,386,650 | 6/1983 | Moen | 165/61 |
| 4,425,810 | 1/1984 | Simon et al. | 374/45 |
| 4,426,619 | 1/1984 | Demand | 324/158 F |
| 4,528,504 | 7/1985 | Thornton et al. | 324/158 F |
| 4,567,432 | 1/1986 | Buol et al. | 324/158 P |
| 4,575,257 | 3/1986 | Ogura et al. | 374/45 |

FOREIGN PATENT DOCUMENTS

| | | | |
|---|---|---|---|
| 397830 | 8/1921 | Fed. Rep. of Germany | 165/61 |
| 2540994 | 8/1984 | France | |
| 0151346 | 11/1981 | Japan | 374/57 |

Primary Examiner—William A. Cuchlinski, Jr.
Assistant Examiner—Thomas B. Will
Attorney, Agent, or Firm—Wallenstein Wagner Hattis & Strampel, Ltd.

[57] ABSTRACT

A temperature conditioning device acheives a fast rate of temperature change in air or gas applied to stress thermally an electronic component by establishing separate cold and hot gas paths from a two-way directing valve interior the device cabinet to a nozzle assembly retaining the gas of selected temperature around the electronic component. An evaporation coil of a mechanical refrigeration system chills the air or gas in the cold gas path interior the cabinet and a tube heater adjusts the air or gas temperature in the cold gas path to that selected. A quartz enveloped nickel-chrome filament heater adjacent the nozzle assembly heats the air or gas in the hot gas path to the temperature selected. A by-pass path in the cabinet continuously convey air or gas around the directing valve to the cold gas path continuously to bathe the cold gas path with chilled air or gas, maintaining the cold gas path ready to supply chilled air or gas and preventing backflow of moist, ambient air to the evaporation coil where the moisture can condense and freeze to block the air or gas flow.

21 Claims, 2 Drawing Sheets

LIVE COMPONENT TEMPERATURE CONDITIONING DEVICE PROVIDING FAST TEMPERATURE VARIATIONS

BACKGROUND OF THE INVENTION

This invention relates generally to devices controlling or conditioning the temperature of an environment in which electronic components are being electrically tested to determine their characteristics at selected or desired hot, cold and intermediate temperatures. Specifically, this invention relates to such devices that bathe the electronic component being tested in a stream of air or nitrogen gas at the selected or desired temperature.

Known devices direct a stream of temperature controlled air onto an electronic component, such as an integrated circuit, that is being tested or is having its electrical characteristics measured. Military standards require testing at −55° C., 0° C., −25° C. and +150° C. These known devices can control the air bathing the electronic component at temperatures from substantially −70° C. to +200° C. at substantially 10 SCFM. Typically, an air supplying cycle between −55° C. and +125° C. has required at least 30 to 45 seconds. This depended on whether the temperature was rising or falling, the mass, heat dissipation and volume of air flow involved. While the cycle times have been acceptable to date, they have slowed the automatic and manual testing of electronic components.

These temperature control devices comprise a rectangular cabinet movable on casters to desired locations in the factory or laboratory. Compressed air is supplied to the cabinet where it is filtered and dried. Alternatively, clean, dry nitrogen gas can be supplied. The clean, dry air or gas then passes through a mechanical refrigeration system where its temperature is lowered to the lowest possible temperature about −70° C. The chilled air then is passed through a flexible tube about ten feet long to a nozzle and the electronic component under test. The tube includes along its length a heater element capable of heating the air or gas to well above the highest temperature desired or to about +200° C. A shroud supports the nozzle above the electronic component and confines the temperature-controlled air around the electronic component. A thermocouple in the nozzle or on the electronic component controls the air temperature.

In these known devices, there is a substantial difference in the time required to change from supplying cold air to supplying hot air compared with the time required to go from supplying hot air to supplying cold air. Changing to supplying cold air is much slower than changing to supply hot air. The reason for this results from the temperature differential or delta T available for heating the air compared to that available for cooling the air.

The tube heater element substantially is a flexible metal tube through which electricity is passed to provide resistance heating of the tube material. The heat from the tube then is conducted into the air passing therethrough. The temperature available from this tube heater element can be much greater than the highest desired testing temperature of about +200° C. Alternative heater elements such as quartz enclosed nickel-chromium filaments easily can produce over +1000° C., if desired. This very great temperature differential provides a very quick change in temperature from cold to hot at a low heater element cost.

The refrigeration system used on the cold cycle, however, provides a much smaller temperature differential, typically a coldest possible temperature of −70° C. for a low temperature test point of −55° C., or a 15° C. differential. The cost of increasing this differential on the cold side is prohibitive, one or two more stages of refrigeration would have to be added to the existing two stages of refrigeration.

Further, the chilled air itself is used to cool the full ten feet or so of tubing including the heating element. Air has a low heat capacity and, coupled with the small cold temperature differential, substantial time is required to cool the tube and nozzle to the desired low temperature. When seeking the desired hot temperature, however, large amounts of electrical power can be used resistively to obtain a desired hot temperature quickly.

These known systems or devices presently operate their refrigeration systems continuously at maximum cooling so there is no additional efficiency or cooling available. It is highly desireable, however, to achieve substantially decreased cycle times without substantially increasing the cost of the device with more refrigeration capacity.

SUMMARY OF THE INVENTION

The invention provides a device capable of cycling air or nitrogen to either extreme of temperature in about five to ten seconds. This substantially reduced cycle time is achieved by separate and parallel hot and cold flow paths from interior the device cabinet to the nozzle assembly positioned over the electronic component under test. A solenoid actuated two-way directing valve inside the device cabinet diverts the air flow through one or the other of the hot and cold flow paths to the nozzle. This changes the previous serial arrangement of the heating and cooling systems to a parallel arrangement and achieves substantially increased cycle times with minimal increased cost.

With the invention, switching from the cold flow path to the hot flow path eliminates the need for heating the air that in the prior devices always had been chilled to the coldest possible temperature. Instead, a high wattage density, low mass, electric heater located at the nozzle assembly provides almost instant hot air from the compressed air or nitrogen gas flowing thereto at approximately ambient temperature. Switching from the hot flow path to the cold flow path eliminates the need to cool the hot electrical resistance heating element. Instead, the chilled air from the refrigeration system cools its flow path tube from about ambient termperature to the desired low temperature.

Additionally, the invention provides a continuous bleeding of a small quantity of air or gas through the cold flow path including the refrigeration system. This continuous passage of cold air or gases maintains the cold flow path tubing at a cold temperature to achieve the almost instantaneous (five to ten seconds) supply of cold (−55° C.) air or gas from the nozzle outlet. This small bleed of air or gas also prevents the backflow of moisture laden ambient air up the cold flow path to the refrigeration coils, where the moisture could condense and freeze, blocking the air or gas flow.

In particular, the device of the invention includes the known cabinet, compressed air filters, dryers and mechanical refrigeration unit. Additionally, the device includes the directing valve located upstream of the refrigeration unit and separate tubing or conduits for the cold and hot flow paths. The cold flow path also includes a low wattage density tube heater, such as was previously used, to heat the chilled air to any desired temperature, typically only to just above ambient. The refrigeration system runs continuously as in the previous devices always to produce air at the coldest possible temperature. The hot flow path includes only a high wattage density heater element, such as a quartz enveloped nickel-chrome filament, to raise the temperature of the air or gas from about ambient to the highest desired temperature. This heater element produces almost instant heating of the gas.

The outlet of the cold and hot flow paths is a nozzle assembly body supported above the component by a shroud and having a pair of ports into which the cold and hot flow paths open and a throat through which the air discharges into a chamber formed by the nozzle body and shroud. Thermocouple temperature sensors in the throat sense the temperature of the air exhausting from the nozzle assembly and surrounding the electronic component.

DESCRIPTION OF THE PREFERRED EMBODIMENT

Figure 1:
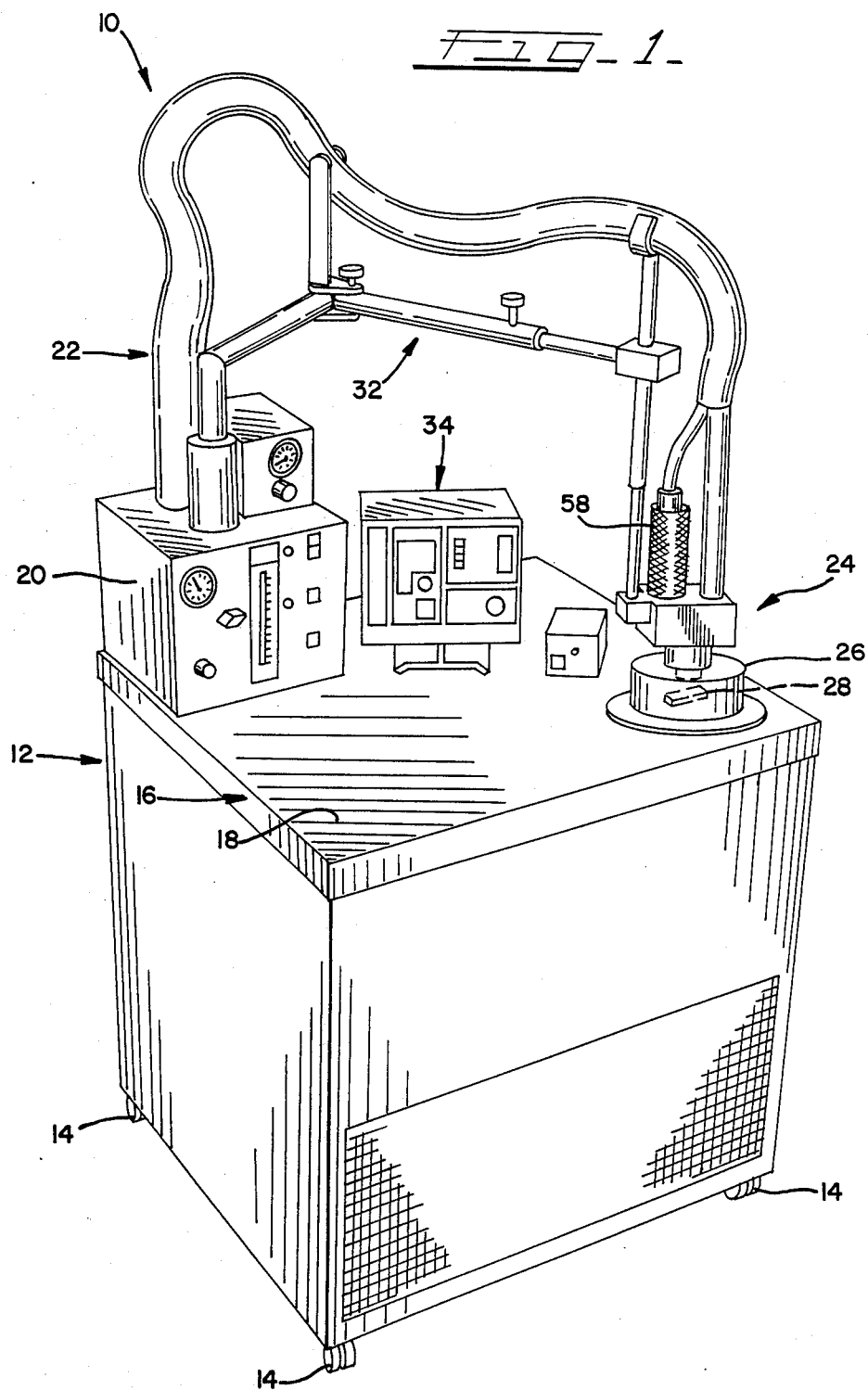
FIG. 1 is a perspective view of a temperature conditioning device including the invention.
Figure 2:
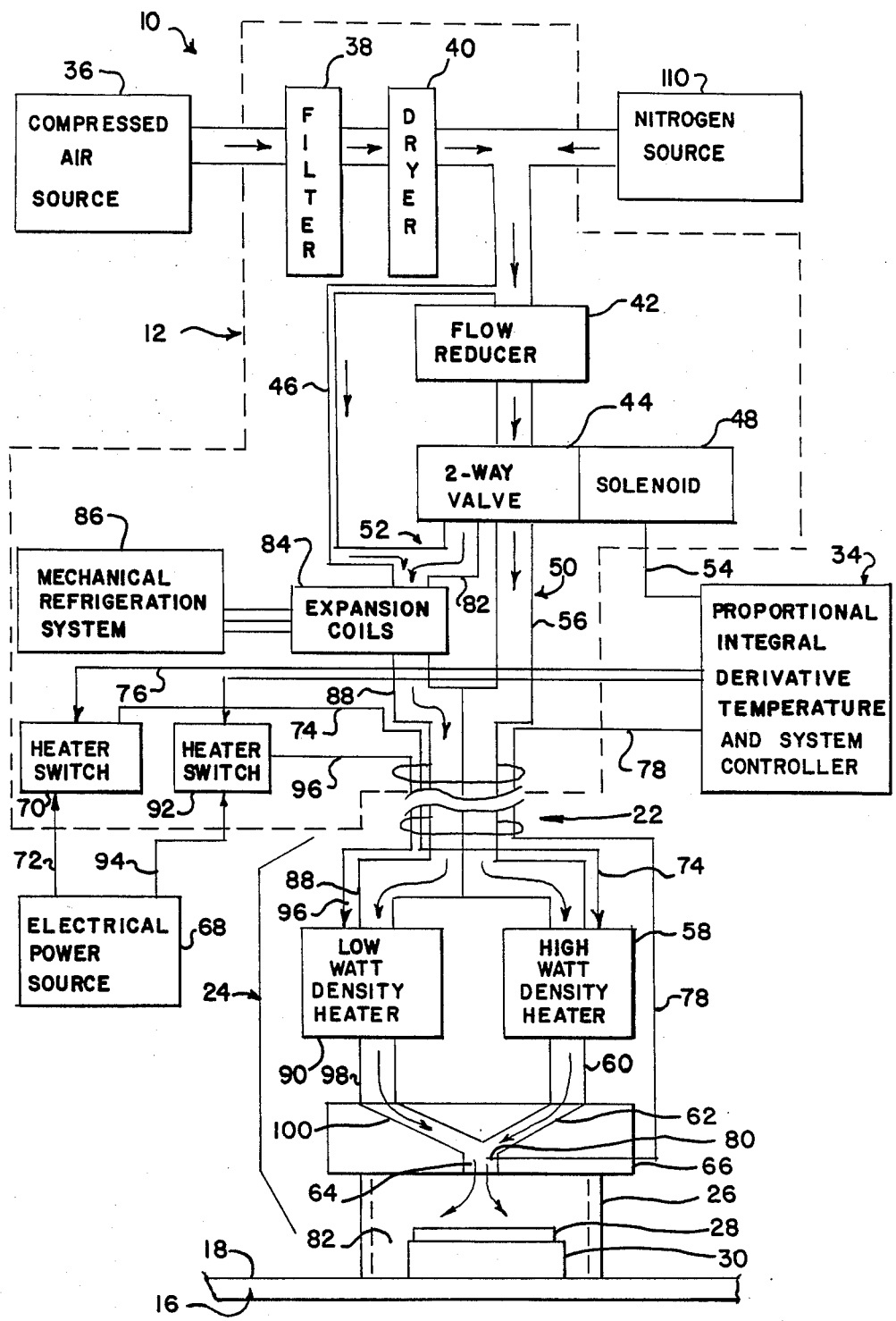
FIG. 2 is a schematic block diagram of the temperature conditioning device including the parallel arrangement of the hot and cold flow paths from interior the device cabinet to the nozzle assembly at the component being thermally stressed.

Referring to FIGS. 1 and 2, a temperature conditioning or thermal stressing device is indicated generally by the reference character 10. Device 10 includes a substantially rectangular cabinet 12 mounted on casters 14 that can be rolled around to any desirable location in a laboratory or factory. Cabinet 12 also includes a cover 16 made of nonconducting laminated material to form a work surface 18. Mounted on cover 16 is an instrument tower 20 from which extends vertically a flexible air stream tube or conduit 22 that terminates in a nozzle assembly 24 above a shroud 26 resting on the top surface 18 of the cover 16. An electronic component such as an intergrated circuit 28 is mounted in a fixture 30 on the top surface 18 of the cover 16 and within the confines of the shroud 26. Conduit 22 is about ten feet long and is suported by any mechanical arrangement desired such as arm assembly 32.

Resting on the top surface 18 of cover 16 and electrically connected to device 10 is an automatic controller 34 that can automatically effect in device 10 manually programmed temperature and rate parameters.

A compressed air source 36 supplies compressed air to device 10. The compressed air passes through a filter 38 and dryer 40 similar to those used in prior devices. Thereafter, most of the clean, dry compressed air passes through flow reducer 42 to two-way directing valve 44. The remainder of the air passes through a tube 46 around the expansion valve and directing valve for purposes to be explained.

The two-way directing valve 44 is controlled by a solenoid 48 to direct the stream of reduced pressure, clean and dry air down either one of separate hot and cold flow paths, 50 and 52 respectively. The solenoid in turn is controlled by system controller 34, over lead 54, which effects the desired manually programmed temperature and rate conditions for the electronic component.

Hot air path 50 includes a tube 56 exiting the cabinet 12 and forming part of flexible conduit 22 extending to nozzle assembly 24 At nozzle assembly 24, the hot air path includes a high wattage density heater 58, such as a commercially available nickel-chrome filament enclosed in a quartz envelope, receiving the air from tube 56 and passing the air through tube 60 to a hot air port 62 and discharge throat 64 of a nozzle body or housing 66. From throat opening 64, the air is enclosed within the shroud 26 to bathe the electronic component 28 with the desired temperature air. High wattage density heater 58 has a low mass and is capable of attaining temperatures as high as 1000° C. in several seconds. This results in almost instantaneous heating of the air passing therethrough and, with the short distance and low mass of the hot air path downstream of heater 58, almost instantaneous bathing of the electrical component in air of the desired hot temperature.

High wattage density heater 58 is supplied with electrical power from source 68, external of cabinet 12, through heater switch 70 over leads 72 and 74. Heater switch 70 in turn is controlled by system controller 34 over lead 76 in response to electrical signals received over leads 78 from a thermocouple 80 located in throat 64 and sensing the temperature of air entering the chamber 82 inside of shroud 26. Alternatively, the thermocouple can be located on fixture 30 or elsewhere as desired. In any event, controller 34 includes a commercially available portion known as a proportional integral derivative temperature controller that programmably senses the rate of change of temperature and adjusts the amount of power applied to heater 58 accordingly to avoid overshooting the desired temperature.

Cold flow path 52 includes a tube 82 conveying air from two-way directing valve 44 to the expansion coil 84 of the mechanical refrigeration system 86 normally present in cabinet 12. Maintaining the expansion coil 84 in cabinet 12 eliminates long coolant lines that otherwise could leak. From expansion coil 84, another tube 88 exits the cabinet 12 and becomes part of conduit 22 extending to nozzle assembly 24.

Along its length, tube 88 includes a low wattage density heater 90 formed by passing electricity through the flexible metal walls of tube 88. Heater 90 works on resistive heating principles and has a large surface area. The air in tube 88 always is lowered to its coldest possible temperature by passing over the evaporation coils of the continuously running refrigeration system, and heater 90 heats the air, typically to a temperature not higher than just above ambient.

Heater 90 is powered from electrical power source 68 through heater switch 92 and leads 94 and 96. Heater switch 92, and heater 90, are controlled by controller 34 in a manner similar to that of heater switch 70 and heater 58. Air in cold air path 52 exits heater 90 and passes through tube 98 to cold air port 100 and throat 64 in nozzle body 66. From throat 64, the air discharges into chamber 82 bathing the electronic component 28 to obtain the desired temperature conditions for testing.

Cold air path 52 is kept in a state of chilled readiness by the small quantity of air, approximately 1.5 to 2 standard cubic feet per minute (SCFM), continuously bled through tube 46. The air bled through tube 46 around flow reducer 42 and two-way valve 44 is received in tube 82 upstream of expansion coil 84. Therefrom, it passes through the expansion coil 84 and the remaining length of cold air path 52 to nozzle assembly 24. The mechanical refrigeration system 86 runs continuously, continuously chilling the bleed air passing therethrough. The chilled bleed air in turn continuously chills the tubing structures of the cold air path, maintaining them in constant readiness to supply larger quantities, substantially 10 SCFM, of chilled air to chamber 82 of nozzle assembly 24 within a few seconds of two-way valve 44 shifting the flow of air down the cold air path.

Additional to maintaining the cold air path chilled, the quantity of bleed air continuously passing through the cold air path prevents moisture laden ambient air from flowing upstream of the cold air path. In the evaporation coil, the moisture can condense and freeze, blocking the flow of air, and requiring the entire system to be shut down to clear the blockage.

In operation, substantially 10 SCFM of air are supplied from compressed air source 36 to flow reducer 42. The hot air path 50 and cold air path 52 provide air exiting nozzle throat 64 at temperatures ranging from −70° C. to +200° C. with a temperature stability of ±1° C. and a temperature stability at the electronic component 28 of ±0.1° C. The separate paths for the chilled air and heated air provide a cycle time of approximately five to ten seconds for producing air exiting nozzle opening 64 from −55° C. to +125° C. or from +125° C. to −55° C. Temperature transition rates can be programmed to be as slow as necessary up to this maximum cycle rate of five to ten seconds. This unusually fast cycle time of the air exiting the nozzle opening 64 results in a 14-pin plastic dual in line package such as integrated circuit 28 going from −55° C. to +125° C. in approximately 20 seconds and going from +125° C. to −55° C. in approximately 40 seconds.

This achievement of fast cycle time results chiefly by separating the chilling and heating functions into two parallel but separate structures, which reduces the mass of either conduit that must be chilled or heated to obtain the desired temperature air in chamber 82. The refrigeration system thus operates substantially separate from the heating system.

Not only are the cycle times between the temperature extremes substantially reduced, but also the energy required to effect such temperature extremes is reduced. Previously, the air exiting the temperature stressing device cabinet 12 always was at the coldest temperature that could be produced, and the air then was heated to the desired temperature by a heating element extending the length of the conduit directing the air to the nozzle assembly. In the present invention, the air entering the chilled air path or the heated air path is of substantially ambient temperature and either is chilled to a lower temperature or is heated to a higher temperature in the separate paths. The refrigeration unit thus does not have to work against the heating system and the heating system does not have to work against the refrigeration system.

The invention thus provides separate heating and cooling paths in parallel with one another to achieve a rapid cycle time from any desired cold temperature to any desired hot temperature or any intermediate temperature thereof.

Modifications and variations of the invention are possible. The particular details of the refrigeration system, including the refrigeration unit 86 and expansion coils 84 can be modified as desired. Heaters 58 and 90 can be provided by any desired heating elements to replace the respective preferred commercially available quartz tube heating element from Sylvania and flexible tube heater. Two-way valve 44 can be any type of valve desired other than the preferred solenoid controlled valve to direct the air substantially to one or the other of the cold air and hot air paths. Alternatively, nitrogen gas 110 can be used instead of air and can be supplied to the system downstream of the filter and dryer. Alternatively, the directing valve and evaporation coil can be located at the nozzle assembly with the high wattage density heater, but this has the drawback of requiring long flexible refrigerant lines that are susceptible of leaking.

I claim:

1. A temperature conditioning device adapted for thermally stressing an electronic component with a gas at a selected temperature other than ambient temperature while obtaining the electrical characteristics of such component, said device receiving said gas from a source and comprising:
 A. cooling means, including an elongate cold gas path, to effect in said gas adapted to be applied to said component said selected temperature substantially at or below said ambient temperature;
 B. heating means, including an elongate hot gas path, to effect in said gas adapted to be applied to said component said selected temperature substantially at or above said ambient temperature, the cooling and heating means being arranged parallel one another and capable of independently of affecting the temperature of said gas;
 C. directing valve means for directing the quantity of gas from said source through one or the other of said cooling means and said heating means;
 D. nozzle means adapted to apply said gas from said heating and cooling means to said electronic component; and,
 E. said cooling means including a by-pass path continuously carrying a small quantity of gas from said source around said directing valve means to said cold gas path.

2. The temperature conditioning device of claim 1 in which said device includes a cabinet containing said directing valve means, said cooling means include a mechanical refrigeration system and an evaporation coil, said evaporation coil being located within said cabinet and said cold gas path including said evaporation coil and extending substantially from said cabinet.

3. The temperature conditioning device of claim 1 in which said device includes a cabinet, said nozzle means are adapted to enclose said electronic component, said heating means include a high wattage density heater that is located adjacent said nozzle means and said hot air path extends from said cabinet to said nozzle means and includes said high wattage density heater.

4. The temperature conditioning device of claim 2 in which said nozzle means are adapted to enclose said electronic component, said cooling means include a low wattage density heater and said cold air path extends from said cabinet to said nozzle means and includes said low wattage density heater downstream of said evaporation coil.

5. The temperature conditioning device of claim 4 in which said low wattage density heater includes a flexible metal tube through which electricity can be passed to form a resistive heating element.

6. The temperature conditioning device of claim 3 in which said high wattage density heater includes a quartz enveloped nickel-chrome filament that can be energized with electricity.

7. The temperature conditioning device of claim 1 in which said directing valve means include a two-way valve actuated by a solenoid.

8. The temperature conditioning device of claim 1 in which said nozzle means include a cold gas path receiving port, a hot gas path receiving port and a single nozzle discharge throat in gaseous communication with said ports for discharging gas therefrom.

9. The temperature conditioning device of claim 1 in which said nozzle means include at least one thermocouple sensing the temperature of gas discharging from said throat.

10. The temperature conditioning device of claim 1 in which said cooling means include an evaporation coil of a mechanical refrigeration system, said evaporation coil is included in said cold gas path and said by-pass path discharges into said cold gas path upstream of said evaporation coil to maintain said cold gas path at a low temperature.

11. A temperature conditioning device adapted for thermally stressing an electronic component carried in a fixture with gas at a selected temperature other than ambient while obtaining the electrical characteristics of such component, said device receiving said gas from a source and comprising:
  A. a cabinet receiving said gas from said source;
  B. a nozzle assembly including a nozzle body and a shroud extending from said nozzle body, said nozzle body and shroud forming a chamber adapted to retain said gas of said selected temperature around said fixture carrying the component;
  C. a cold gas path capable of being in gaseous fluid communication with said source in said cabinet and extending to said nozzle assembly, said cold gas path including the evaporation coil of a mechanical refrigeration system capable of effecting the lowest selected temperature in said gas, a by-pass gas path that directly and continuously conveys said gas from said source to said cold gas path upstream of said evaporation coil to maintain said cold gas path at a cold temperature;
  D. a hot gas path capable of being in gaseous communication with said source in said cabinet, being separate from said cold air path and extending to said nozzle assembly, said hot gas path including a first heater capable of effecting the highest selected temperature in said gas; and,
  E. said cold gas path and hot gas path both being in gaseous fluid communication with said chamber of said nozzle assembly.

12. The temperature conditioning device of claim 11 including a valve receiving said gas from said source and directing said gas to one or the other of said cold gas path and hot gas path.

13. The temperature conditioning device of claim 12 in which said valve is contained in said cabinet.

14. The temperature conditioning device of claim 11 including a valve receiving said gas from said source and directing said gas to one or the other of said cold gas path and hot gas path, and said by-pass path extending around said valve from upstream said valve to said cold gas path.

15. The temperature conditioning device of claim 14 which said valve and by-pass path are contained in said cabinet.

16. The temperature conditioning device of claim 11 in which said evaporation coil is contained in said cabinet.

17. The temperature conditioning device of claim 11 in which said cold gas path includes a second heater capable of heating said gas from the lowest selected temperature to desired temperature.

18. The temperature conditioning device of claim 17 in which said second heater is downstream of said evaporation coil.

19. The temperature conditioning device of claim 11 in which said first heater is adjacent said nozzle assembly.

20. The temperature conditioning device of claim 11 in which said nozzle assembly includes one cold gas port receiving gas from said cold gas path, a second hot gas port receiving gas from said hot gas path and a discharge throat in gaseous fluid communication with said two ports for discharging gas into said chamber.

21. A temperature conditioning device adapted for thermally stressing an electronic component carried in a fixture with a gas from a source at a selected temperature while obtaining the electrical characteristics of such components, said device comprising:
  A. a cabinet;
  B. a two-way directing valve located in said cabinet and receiving said gas from said source, said valve directing said gas down one of a cold gas path and a hot gas path, which are separate and parallel one another;
  C. an evaporation coil of a mechanical refrigeration system contained in said cabinet, said evaporation coil being capable of effecting the lowest possible selected temperature in said gas and being downstream of said valve in said cold gas path;
  D. a by-pass path continuously conveying gas from said source to upstream said evaporation coil in said cold gas path around said valve so that there is a continuous flow of cold gas through said cold gas path;
  E. a pair of flexible tubes extending from interior said cabinet to exterior said cabinet, one cold gas tube receiving chilled gas from said evaporation coil and carrying said cold gas path and the other hot gas tube receiving gas from said two-way directing valve and carrying said hot gas path, said cold gas tube including a low wattage density heater capable of heating said gas from the lowest possible selected temperature to the selected temperature;
  F. a high wattage density heater receiving the gas from said hot gas tube carrying said hot gas path and capable of heating said gas to the highest possible selected temperature; and
  G. a nozzle assembly coupled to said one tube and said high wattage density heater, said nozzle assembly including a nozzle body and a shroud forming a chamber extending therefrom, said nozzle body having one port receiving said cold gas path, a second port receiving said hot gas path and a discharge throat for discharging gas from said two paths into said chamber, said chamber adapted to contain said gas at said selected temperature around said electronic component.

* * * * *